(12) United States Patent  
Armstrong

(10) Patent No.: US 6,513,720 B1  
(45) Date of Patent: Feb. 4, 2003

(54) PERSONAL ELECTRONIC STORAGE DEVICE, CONTAINER, AND LABELING

(76) Inventor: Jay A. Armstrong, 6127 DeSoto Dr., Colorado Springs, CO (US) 80922

(*) Notice: Subject to any disclaimer, the term of this patent is extended or adjusted under 35 U.S.C. 154(b) by 102 days.

(21) Appl. No.: 09/702,997

(22) Filed: Oct. 30, 2000

Related U.S. Application Data

(63) Continuation of application No. 09/146,799, filed on Sep. 3, 1998, now Pat. No. 6,140,936.

(51) Int. Cl.[7] .............................................. G06K 19/06
(52) U.S. Cl. ...................... 235/492; 235/486; 235/487
(58) Field of Search ................................ 235/492, 487, 235/486

(56) References Cited

U.S. PATENT DOCUMENTS

| | | |
|---|---|---|
| 3,958,690 A | 5/1976 | Gee, Sr. |
| 3,970,996 A | 7/1976 | Yasaka et al. |
| 4,197,665 A | 4/1980 | Sitter |
| 4,259,391 A | 3/1981 | Brecht |
| 4,491,725 A | 1/1985 | Pritchard |
| 4,745,268 A | 5/1988 | Drexler |
| 4,795,898 A | 1/1989 | Bernstein |
| 4,816,653 A | 3/1989 | Anderl et al. |
| 5,161,826 A | 11/1992 | Van Giesen et al. |
| 5,171,039 A | 12/1992 | Dusek |
| 5,197,763 A | 3/1993 | Whalen |
| 5,291,399 A | 3/1994 | Chaco |
| 5,325,294 A | 6/1994 | Keene |
| 5,499,293 A | 3/1996 | Behram |
| 5,590,038 A | 12/1996 | Pitroda |
| 5,622,429 A | 4/1997 | Heinze |
| 5,658,016 A | 8/1997 | Goeken |
| 5,674,252 A | 10/1997 | Morgan et al. |
| 5,675,744 A | 10/1997 | Tsujii |
| 5,680,864 A | 10/1997 | Morgan et al. |
| 5,708,851 A | 1/1998 | Togawa |
| 5,936,542 A | 8/1999 | Kleinrock et al. |

*Primary Examiner*—Harold I. Pitts
(74) *Attorney, Agent, or Firm*—John R. Wahl; Merchant & Gould P.C.

(57) ABSTRACT

An electronic data storage device is described that is capable of being worn, such as, as a piece of jewelry. The device includes a memory card, a modifiable directory structure for organizing electronic files stored in the memory card, modifiable electronic files containing bearer information stored in the directory structure, and may have a container enclosing the card and/or covering card contacts. The device may include labeling on one of an exterior surface of the memory card and/or the container indicating a name of the bearer to whom the information pertains; and unique data identifying the bearer retrievably stored on said memory card. The memory card may be inserted in an adapter and information retrieved and read via a personal or laptop computer.

20 Claims, 7 Drawing Sheets

PERSONAL ELECTRONIC STORAGE DEVICE, CONTAINER, AND LABELING

CROSS REFERENCE TO RELATED APPLICATIONS

This application is a continuation of U.S. patent application Ser. No. 09/146,799, filed Sep. 3, 1998, U.S. Pat. No. 6,140,936.

BACKGROUND OF THE INVENTION

1. Field of Invention

The present invention relates to a compact electronic document storage device which may be carried by people or animals. More specifically, the present invention relates to an electronic data storage device used for dynamic information storage and retrieval of text and documents.

2. Prior Art

Original medical and veterinary data and images are typically kept on paper or photographic media. While individuals may obtain copies of such records from health care and veterinary providers, these records may not be centrally located.

Even if a bearer can locate all such records and obtain copies of the originals on the same media, they are cumbersome and may be easily damaged. When people or animals travel away from their primary domicile, they may need access to their medical or veterinary records, but carrying all of the records with them wherever they go is impractical. This is especially true for people or animals engaging in rigorous physical activities such as sports, firefighting, police work, and military combat.

Furthermore, there is no widely-accepted standard way of organizing documents so that medical and veterinary professionals know where to quickly place or retrieve needed documents.

In order to provide background information so that the invention may be completely understood and appreciated in its proper context, reference is made to a number of prior art patents, publications, and information as follows:

U.S. Pat. No. 3,958,690 is a medical information and medication package with folding card and printed instructions in an envelope. While useful, this invention is easily damaged and hard to carry and it is not intended to be worn as a jewelry item.

U.S. Pat. No. 5,197,763, a biomedical information card and method of making, refers to a kit so that individuals can create their own emergency medical data card which is "slightly smaller than a credit card" and is "attached to a blank rigid plastic card". U.S. Pat. Nos. 5,171,039 and 4,745,268 refer to "wallet-size" cards. U.S. Pat. No. 4,816,653 is a portable data carrier for "individual medical and/or banking records" which "looks and feels much like an ordinary credit card." Again, these are easily damaged and are not intended to be worn as a jewelry item.

U.S. Pat. No. 4,491,725 is a medical insurance verification and processing system which reads a "medical information card (MEDICARD)" to "determine a patient's background medical and insurance information." This system is specifically for insurance processing and specific reference is made to transmitting information to a "central brokerage computer". The card does not necessarily carry complete patient records and images for the bearer.

U.S. Pat. No. 5,590,038 is a "universal electronic transaction card" which is capable of serving as a number of different cards including "credit cards, bank cards, identification cards, employee cards, medical cards, and the like." The user can press graphical images on the card to select the card type. The specific use as a medical card is not elaborated, nor its use in harsh conditions, nor its being worn as jewelry.

Credit-card-size emergency medical cards may be used to store medical data as printed text and images on plastic and paper media and the like, but they are limited in the amount of printed area, are easily damaged, and such cards are not easily distinguishable from other cards carried by the bearer. Credit-card and wallet-size devices are not easily worn as jewelry.

U.S. Pat. No. 4,197,665 is an identification locket with "an information bearing card" in a substantially reduced form" and which has a magnifying lens. While it can be worn as jewelry, magnifying devices are needed and the amount of information stored on the card is still very limited. Further, this invention is not necessarily for harsh environments.

Emergency medical tags and pet tags indicating critical medical conditions and personal data may be worn, typically on a necklace, collar, bracelet, or wristband, but only a small amount of data may be displayed on the surface of such tags.

Images of medical documents may be reduced and stored on microfilm. U.S. Pat. No. 4,259,391 is an identification card with transparent laminate using microfilm. Microfilm cards may be carried as is or attached to emergency medical cards, but such film is easily damaged. In addition, reading microfilm images generally requires an optical magnifying device.

The aforementioned medical cards, tags, and microfilm cannot be easily reused. When the relevant data changes, a new card, tag, or microfilm image is needed.

Documents containing only text may be manually converted to electronic text format or by using optical character reader (OCR) devices or OCR computer software.

Documents and images may be scanned into electronic image format and stored in electronic files. Typical formats for these image files are BMP (bitmap), JPEG, and GIF, though there are many other formats.

Electronic files may reside in a single electronic directory or organized in multiple directories. Each directory folder may be named to indicate which type of electronic files are stored therein. However, there is no standard or widely recognized format for an electronic directory structure for organizing medical or veterinary files carried by the owner to whom the files pertain.

Once in electronic format, files may be saved on mass data storage devices, such as disk drives and magnetic tape. The files may be transferred to floppy diskettes or magnetic tape reels and cartridges, but these are still generally too large for personal conveyance as they will not fit easily in a wallet or purse, nor can they be easily worn like jewelry on a necklace or bracelet.

In addition, disk drives, diskettes and tapes are generally susceptible to damage. Protective containers and ruggedization schemes only serve to make them more unwieldy.

Medical research efforts often require collecting medical history and data from a large set of human beings. A unique medical identification number, similar to a Social Security Account Number (SSAN) number has been proposed to provide a means for collecting data; however, such an identification system is intrusive to personal privacy and assigns unnecessary control to government bureaucracy. A means of quickly collecting medical history from a large number of subjects without compromising personal privacy is needed.

Research and businesses involving animals often involve tagging animals. Transmitters and numeric tags are attached to the animal with a strap, or by puncturing the skin, or by other suitable means. However, transmitters may quit functioning due to power loss or damage, and tags contain only a small amount of written data. For larger animals, a diskette or tape cartridge, for example, could be placed in a protective container and attached to the animal; however, for smaller animals, such as migratory birds and fish, attaching a diskette or tape cassette would severely impede the animal's normal activities.

Electronic files on diskettes and disk drives may be accidentally erased, overwritten, or intentionally accessed without the permission of the owner. Floppy diskettes sometimes have a "write protect" switch. Some computer operating systems and file systems allow for protections to be set for particular electronic files or directories. These protections can require passwords for accessing protected files and directories.

U.S. Pat. No. 5,325,294 is a medical privacy system which uses an identification card with a photograph or holographic image and a "visually perceptible" "first identification number" which is associated with a "confidential second identification number" on a computer database. This system associates two numbers, but does not use data encryption nor file system password protections. Further it specifies that the actual data is available via a "telephonic readout" implying that the data is not on or in the card itself. Further, there is no tissue sample of the bearer for DNA, blood type, or other physical comparison for positive identification.

Data may be stored on electronic memory cards. U.S. Pat. No. 4,795,898 is for a "personal memory card the size of a standard plastic credit card." This device receives power from an external signal.

U.S. Pat. No. 3,970,996 is an apparatus for collecting medical data which basically collects data from an ID card and prints it. There is no provision for use in harsh conditions. Further, neither the size of the card nor for the amounts and types of data stored on the card are specified. There is no provision for use on common personal computers.

U.S. Pat. No. 5,675,744 is for a medical service workstation and includes an "optical card carried by the patient" and read through an ISDN interface. Similarly, U.S. Pat. No. 5,708,851 is a system for managing medical information using a "hybrid card" with an "optical stripe." U.S. Pat. No. 5,622,429 utilizes a memory card for transferring data between operating room equipment. These cards are not intended for harsh conditions, for storage of complete medical records and images, nor for personal use, nor for wear as a jewelry item.

Small electronic storage devices have been invented for storing electronic images taken with digital cameras. Commonly called "flash memory", these devices come in four standard types: PCMCIA (Personal Computer Memory Card International Association),CompactFlash™ (CF™) (by SanDisk Corporation), Miniature Card (by Intel® Corp.), and SmartMedia™ (also known as SSFDC) (by Toshiba).

The largest of these is PCMCIA, which is credit-card size. All PCMCIA cards have a standard length and width (85.6 mm×54.0 mm, or 3.3 inches×2.13 inches), but have different thicknesses: Type I is 3.3 mm, Type II is 5.0 mm, and Type III is 10.5 mm thick. All three types use the same type of 68-pin connector. The PCMCIA standard provides for 3.3 Volt and 5.0 Volt operation. The Type IV specification is believed to be under development and is expected to be 18.0 mm thick.

PCMCIA card reader devices are a common feature on many laptop computers, and card reader devices are available as an option on some desktop computers and palmtop computers.

U.S. Pat. Nos. 5,674,252 and 5,680,864 suggest a PCMCIA format card for gathering event data with a time stamp from an instrument clock. The purpose is not for personal transportation of medical files in harsh conditions.

U.S. Pat. No. 5,499,293 is for data compression/decompression and makes reference to "medical information storage and retrieval" and a "SmartCard based system." The purpose of this invention was to make data fit within the limited memory of a variety of devices, and the abstract makes specific reference to "this card based system . . . from a credit-card sized instrument." Credit card sized cards may fit nicely into a wallet or purse, but are too large to be worn conveniently as jewelry items.

U.S. Pat. No. 5,291,399 is a portable personal database as for a hospital environment which uses memory cards. The size of these cards could be quite large and are not necessarily carried by the person to whom the card's data pertains. Further, this system is specifically for "a hospital environment", not harsh conditions.

Though they are credit-card sized, PCMCIA cards are still too large to be worn comfortably on a necklace or wristband, particularly if they are in protective containers. CompactFlash™, SmartMedia™, and Miniature Card are considerably smaller than PCMCIA devices, and are small enough to be worn comfortably; however they lack attachment points. CompactFlash™ cards have approximate dimensions of 45 mm×36 mm×3.3 mm (5346 cubic mm), SmartMedia™ have approximate dimensions of 45 mm×37 mm×0.76 mm (1265.4 cubic mm), and Intel® Miniature Card cards have approximate dimensions of 38 mm×33 mm×3.5 mm (4389 cubic mm).

Flat surfaces of such cards can be used as attachment points, but attaching directly to the card can damage it or affect its ability to be inserted into a card reader device. U.S. Pat. No. 5.161,826 is a "composite medical information and identity card" which is "permanently heat sealed". Such heating is likely to damage an electronic device.

In addition, card slots to read these devices are not generally provided on personal computers, as it would be expensive to provide all three types plus PCMCIA.

Via adapters, CompactFlash™, SmartMedia™, and Intel® Miniature Card may be used in PCMCIA card slots. All types can store electronic files compatible with personal computer operating systems. Some cards are ATA (AT Attachment, or Advanced Technology Attachment) compliant and so can be used directly with some computer operating systems. Linear (or "non-ATA") cards require special device drivers called Flash File System (FFS) or File Translation Layer (FTL) software. Because these drivers have different versions which are not always compatible with different systems, data cannot always be transferred from one device to another.

Generally, the flash memory cards are shock resistant and may provide some heat, moisture and dust resistance, but they are generally not designed for extremely dusty, sandy, corrosive, high pressure or other harsh conditions, nor for submersion in liquids. Further, electromagnetic interference (EMI) from electronic devices and electromagnetic pulses (EMP) and radiation from radioactive materials and nuclear detonations can damage the electronic files stored on a memory chip.

A further shortcoming is that there is no summary of important bearer treatment data on the exterior of the device nor on a container for the device. There is no exterior label or case which indicates that the card contains electronic medical or veterinary documents nor treatment information.

Most cards come with a blank label already affixed to the card and upon which the bearer's name and other data may be written; however, unlike a sheet of paper, the card cannot be placed in a printer for printing more complex and precise text and images.

There is no photographic image and other identifying data on the exterior of the memory cards. This disadvantage would prevent, for example, an emergency medical technician from easily distinguishing the device as a repository of medical or first aid data for the bearer.

U.S. Pat. No. 5,658,016 is an attachment for an identification card with an "attention strip" alerting the user that information "such as medical information" is available on the rear of the card.

Whatever the precise merits, features and advantages of the above cited references, none of them achieves or fulfills the purposes of the personal electronic document storage device, directory structure, labeling, and container.

OBJECTS OF THE INVENTION

A principal object of the present invention is to provide a means for easily and safely carrying electronic data, documents, and files in a long-lasting, reusable compact device which is small enough to be worn like jewelry, and yet is capable of withstanding harsh conditions.

Another key object of the present invention for storing text, image, and multimedia audio and video files on the device.

Another object of the present invention is to store programs for editing, viewing, and playing text, image, and multimedia files on the device.

Another key object of the present invention is that it can be quickly inserted in personal computers, including portable and handheld computers, that the computer operating system automatically detects the presence of the device and the device's file system, and that the files can be quickly accessed, read, created, removed and changed by an operator.

A further object of the present invention is for the device to have an electronic directory structure which is organized for quick access of electronic files by medical and veterinary professionals.

Yet another object of the present invention is to make the device easily recognizable as containing information pertaining to medical or veterinary treatment for the bearer.

Still another object of the present invention is to prevent illicit access to and use of memory chip contents.

An elementary object of the present invention is the ability to quickly collect a subset of data from a large number of bearers for the purpose of studies which do not compromise the privacy of the individual bearers.

SUMMARY OF THE INVENTION

In fulfillment and implementation of the previously recited objects, as well as other objects which will become apparent from the discussion which follows, a primary feature of the invention resides in providing a means of safely creating, carrying, organizing, identifying, and retrieving electronic medical and veterinary data and documents in a small, easily carried, reusable, ruggedized device. A case containing the device provides protection from the elements and means of attachment to wristbands, bracelets, necklaces and the like. Labels identifying the bearer, displaying critical treatment data, and indicating that the device holds medical or veterinary documents and images are integrated with the surfaces of the device and the container. Electronic files are organized in an easily traversed directory structure. Private files and directories are protected with encryption techniques and passwords.

These objects, as well as other objects which will become apparent from the discussion that follows, are achieved, according to the present invention, by obtaining electronic files which contain medical data, forms and images and storing them on a suitably small memory chip with sufficient storage space. Labels indicating that the chip contains medical or veterinary information and showing the bearer's identity and important treatment data are affixed to the memory card. Similar labels are affixed to a protective container which also serves as a means of attachment for bracelets, necklaces, wristbands, watches, pendants, and the like.

There are many ways to create electronic documents. Typically, records with images and charts on photographic or paper media, such as x-rays, Magnetic Resonance Images (MRIs), EKG charts and so forth, would be scanned directly into electronic image files. Text files can also be stored in image files, but image formats, such as JPEG, BMP, and GIF, generally take up more storage space than text files, and so, unless an image is required for signatory evidence, legal or other purposes, records containing only text would generally be processed with an optical character reader device or software and saved in text format, such as an ASCII text file.

Electronic documents may also be composed and edited with computer word processing and image editors. For example, a prescription can be edited via a word processor.

In addition, multimedia files, such as voice or video instructions for filling and taking a prescription, can be put in electronic files. For example, a doctor or nurse could state instructions into a microphone and before a video camera, and an electronic multimedia file saved on the memory card for future playing.

Once files are in electronic or text format, the memory chip, which is compatible with a computer's operating system and file system, is inserted into a device connected to the computer which can read and write electronic files on the memory chip.

Some "plug and play" operating systems automatically detect the presence of the memory card, and make its contents available to the user.

A computer operator then creates a directory structure on the memory chip with directories for the bearer's name, identification information, emergency data, organ donor information, images, types of images, contact information, military data, prescriptions, medications, insurance and billing information, in-patient records, out-patient records, and so forth. This directory structure follows a standardized format with an easily traversed structure and appropriate naming for directories and files, so that files may be retrieved quickly by emergency personnel.

The computer operator then copies the electronic documents into the appropriate directories in the standard directory format. For example, the highest directory in the hierarchy would be named with the bearer's name. The bearer's contact data (phone number, address, etc.) would be placed in a file called "Contact Data". An electronic text file showing in-patient treatment records would be copied to the in-patient record directory. An x-ray image file would be copied to the x-ray subdirectory under the images subdirectory.

The operator would then select any files requiring encryption and encrypt them with an encryption utility. Encryption keys would be provided to the bearer or the bearer's guardian, so that the bearer or guardian can control access to private files.

If the operating and/or file system allows it, password protections can be placed on files and directories so that the bearer or guardian can prevent undesired access.

Executable computer programs in whole or in part could also be copied to the directory structure. For example, image viewer programs can be copied to a directory so that, if other computers do not have the viewer programs, they can be obtained from the chip.

A photographic image of the bearer and an image of the bearer's fingerprint would be scanned into electronic format. These images would be saved in electronic files on the memory chip and printed onto one or more rugged labels, along with the bearer's identity and critical treatment data. The labels are affixed to the memory chip and to protective containers for the chip.

A hair strand, bodily fluid sample, or other tissue sample from the bearer containing DNA (deoxyribonucleic acid) can also be attached to the surface of the chip for DNA testing and verification of identity.

Chips with labels can be carried by the bearer in a wallet, pocket or purse, or in containers worn as jewelry. Containers which have attachment lugs or surfaces for adhesives, can be attached to wristbands, necklaces, or other jewelry items for wearing by the bearer.

The container is designed to protect the memory card from the effects of harsh or hostile environments. Depending upon the bearer's needs, it can protect against nuclear radiation and electromagnetic pulse, as well as shock, dirt, dust, corrosive materials, submersion in liquids, and other potentially damaging conditions.

If the bearer is injured and rendered unconscious, say in a boating accident or military combat, emergency treatment personnel can check the bearer's body for a card, looking for the symbols indicating medical information on the memory card and/or container.

After verifying that the photograph on the card's labeling pertains to the bearer, treatment personnel can examine the card's labels for emergency treatment data, such as blood type, allergies and disorders. The card can be quickly inserted into a handheld or laptop computer and more detailed information can be immediately obtained. For example, the bearer's recent history of prescriptions taken can be quickly examined and treatment rendered accordingly.

The bearer can carry the memory card to a pharmacy where personnel can plug the chip into a computer and fill the order, reading the prescription as printed text instead of less legible handwriting.

Multimedia audio and video files on the chip can be replayed at home or at other treatment locations. Programs for editing, viewing and playing electronic text, image and multimedia files may be stored on the memory chip.

The electronic files can also be quickly transferred to remote locations for obtaining additional treatment opinions, advance preparation for treatments, and organ donor programs.

For controlled access, fingerprints, retina scans, DNA data, holographic images, and/or photographic images can be placed on the labeling and/or stored in an encrypted electronic file. These files and images can be used to verify that the memory card does, in fact, pertain to the bearer. Such verification can prevent fraudulent provision of medical services and medications.

For the deceased, organ donor information and next of kin would be immediately accessible. The memory card and identification data could also be used to identify badly decomposed bodies.

If the bearer's medical history or relevant data changes, the reuseable card can be reinserted into a device for updating, adding, and deleting data, images, and documents.

If the bearer's card is lost, a replacement card with labels can be created by downloading duplicate electronic files kept on a diskette, disk drive, file server or other repository, and placing the backup files on a new memory chip.

Similarly, if a bearer's chip runs out of storage space, the files can be transferred to a chip with greater memory capacity.

Should a study or research be conducted requiring data from a set of bearers, relevant data can be quickly collected without the bearers having to reveal private data. This utility obviates the need for a centralized database controlled by a government agency, large corporation, or other organization which intrudes into individual privacy.

Similarly, animal studies and control can be improved by attaching cards to subject animals and updating the stored data as needed. For example, data related to animal diseases could be quickly obtained by collecting data from memory cards carried by subject animals. The history of veterinary care for cows, pigs, and other such food sources could be more easily tracked.

The foregoing and other objects, features and advantages of the invention will be apparent from the following more particular description of the preferred embodiments of the invention, as illustrated in the accompanying drawings.

DESCRIPTION OF PREFERRED EMBODIMENTS

The invention may be embodied in many different ways. The preferred embodiment of the invention is not limited to the following description.

A CompactFlash™ memory card, which is less than 5,500 cubic millimeters in volume. The card's two largest surfaces, 1 and 2, have labels affixed. The smaller sides, 3 and 4, could have narrow labels, but side 3 has a connector with numerous holes for the pins which should not be covered by permanent labeling.

Labels 5 and 9 are each the internationally recognized symbol for first aid. Labels 6 and 10 are each the internationally recognized symbol for information.

Label 7 has the bearer's name (for illustration, the card shown is for Abe Lincoln). Label 7 also has important treatment information such as the bearer's blood type, allergies, and disorders. Label 8 is a photographic quality image of the bearer (again, for illustration, Abe Lincoln).

Figure 1:
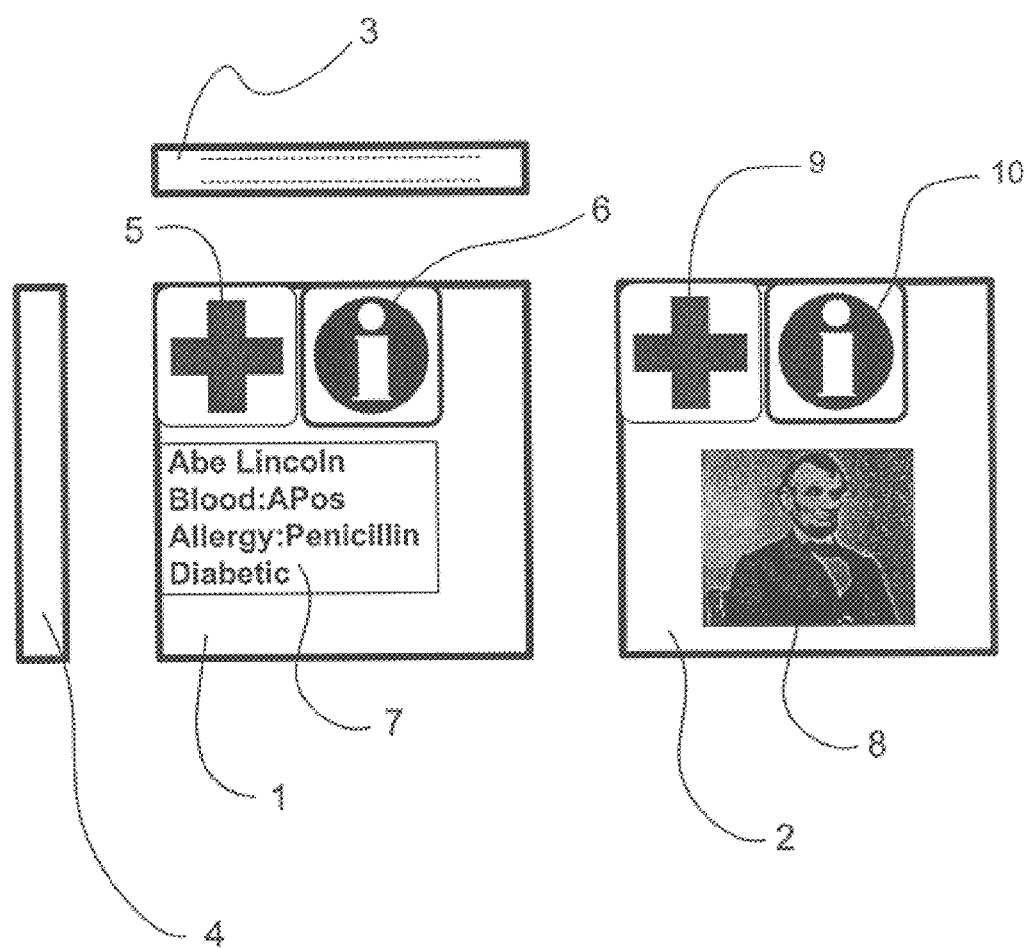
FIG. 1 illustrates a preferred implementation of memory cards with exterior labeling.
Figure 2:
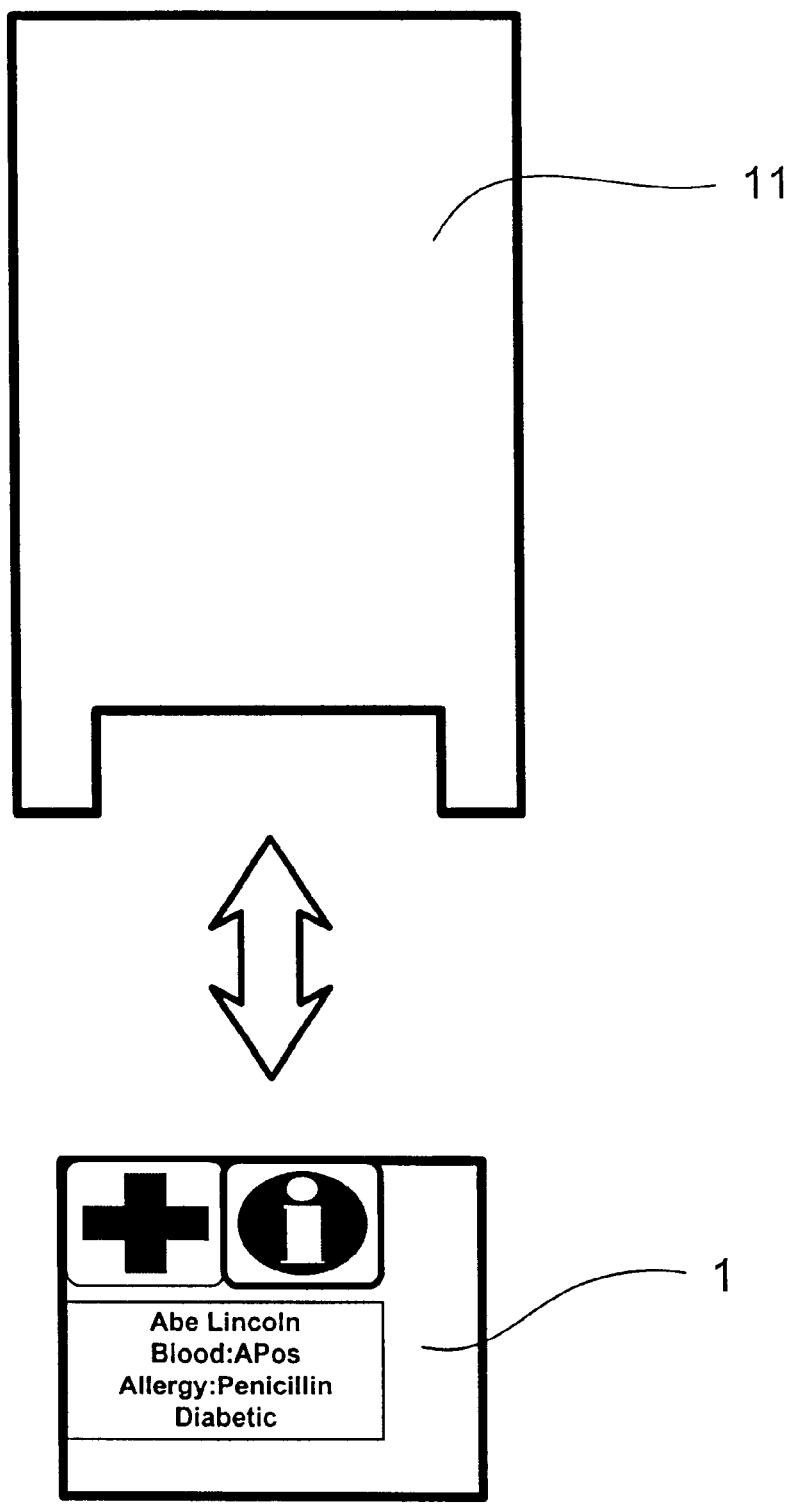
FIG. 2 illustrates how a memory card can be inserted into a PCMCIA adapter.
Figure 3:
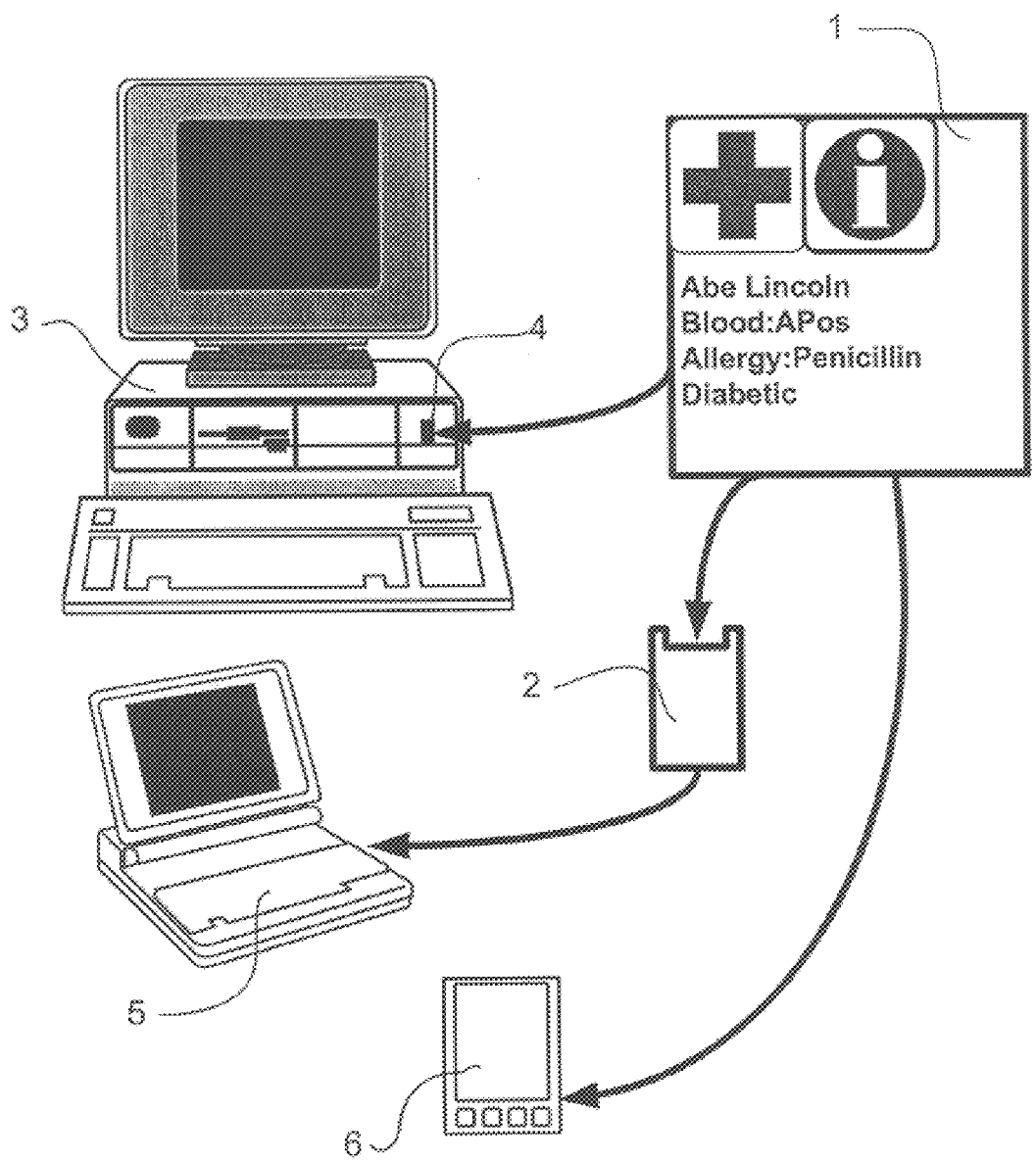
FIG. 3 illustrates how a memory card might be used in different personal computers, laptop computers, and handheld computers.

The memory card may be inserted into a PCMCIA adapter 11 shown in FIG. 2 and FIG. 3. Depending upon which types of card readers exist on a computer, a PCMCIA adapter may or may not be necessary. The adapter with memory card may then be inserted into a PCMCIA card slot, such as on a personal computer, 12, a laptop computer 14, or a palmtop computer 15.

The card may be inserted directly into a card reader device which is attached to or an integral part of a computer. FIG. 3 shows a card being inserted directly into a personal computer 12 which has a card reader 13, or inserted directly into a palmtop computer 15.

Figure 4:
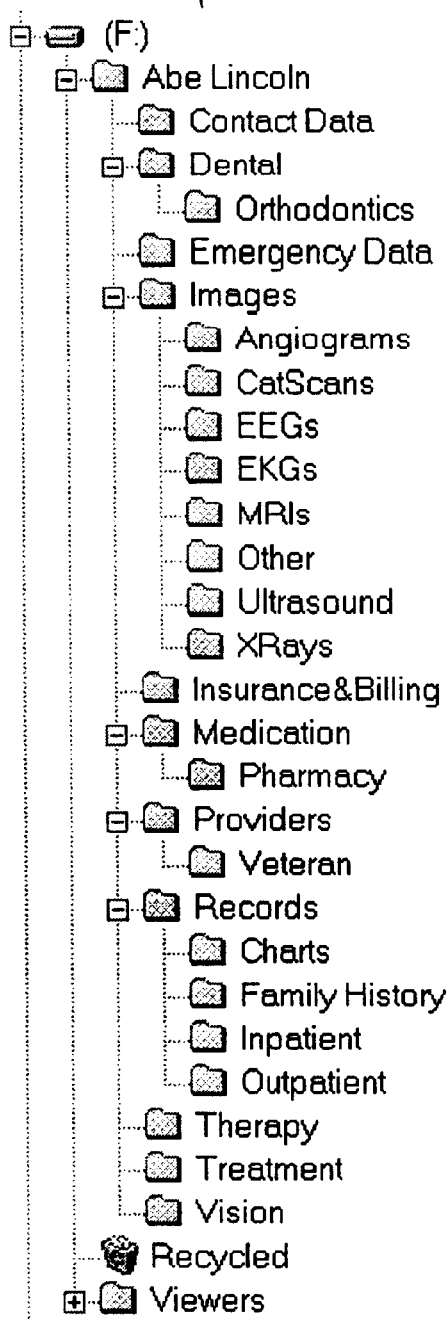
FIG. 4 illustrates an electronic directory structure.

Once in a computer, the files may be created, edited, viewed, deleted, and so forth. The directory structure 16 shown in FIG. 4 is used to facilitate locating files. The directory structure shown is for an actual CompactFlash™ card inserted into a PCMCIA card slot on a laptop computer. The computer operating system is Microsoft® Windows95©. The card is automatically recognized as an ATA (AT Attachment) disk and displayed as drive "F:", with directory tree as shown.

Figure 5:
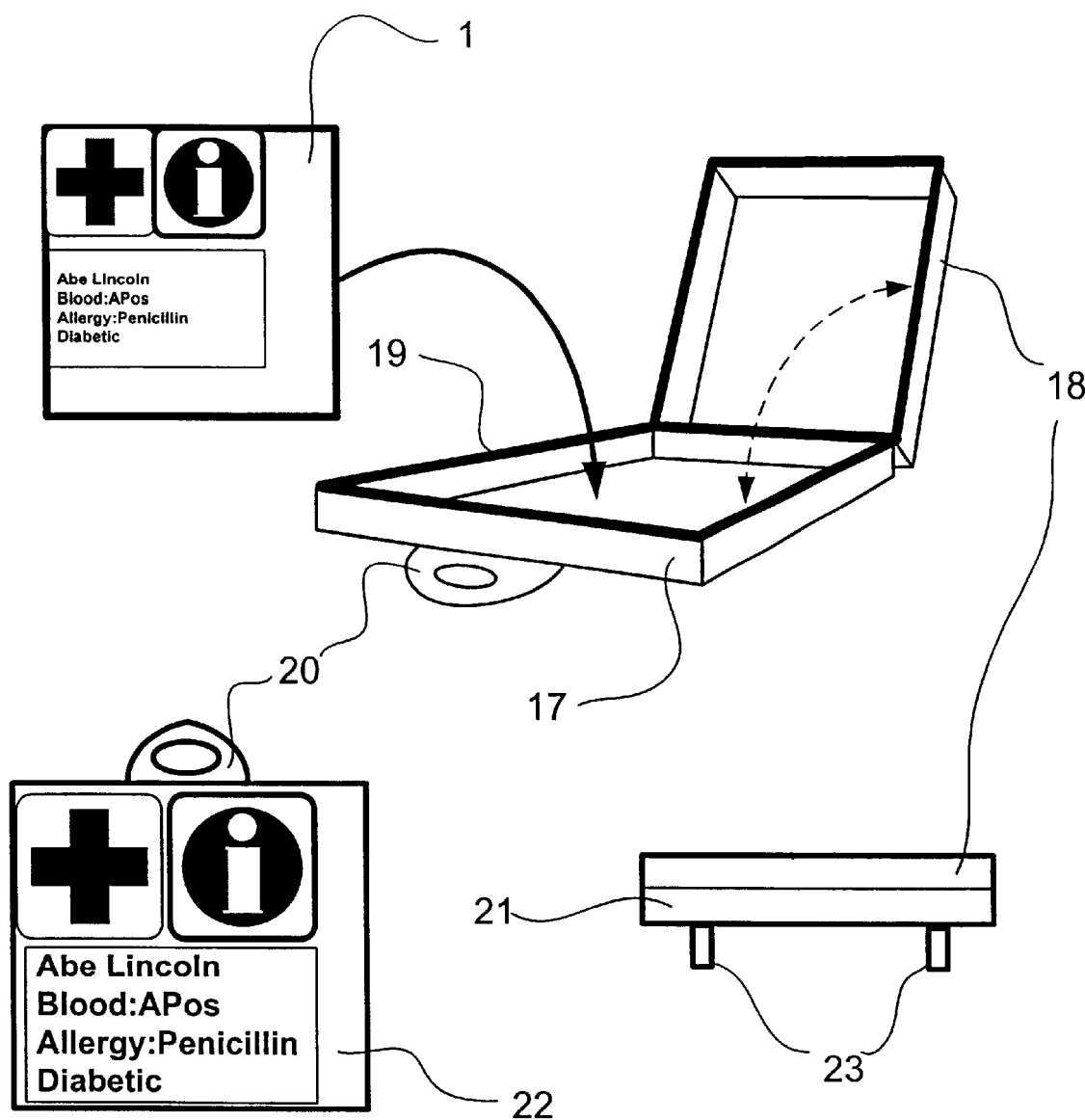
FIG. 5 illustrates a container for memory cards with attachment points and surfaces, and shows how a card can be placed in such a container.

FIG. 5 shows a container to carry the card on a bearer's body. The container has a bottom 17, a lid 18 and a seal 19 to protect against the elements. A lug 20 serves as a means of attachment to necklaces, chains and the like. Side view 21 shows lugs 23 for attachment to a watchband, bracelet or the like. A top view 22 shows lug 20 and labeling as previously described.

The container is resistant to shock, pressure, dust, moisture, corrosion, EMI/EMP, and radiation from radioactive materials.

Figure 7:
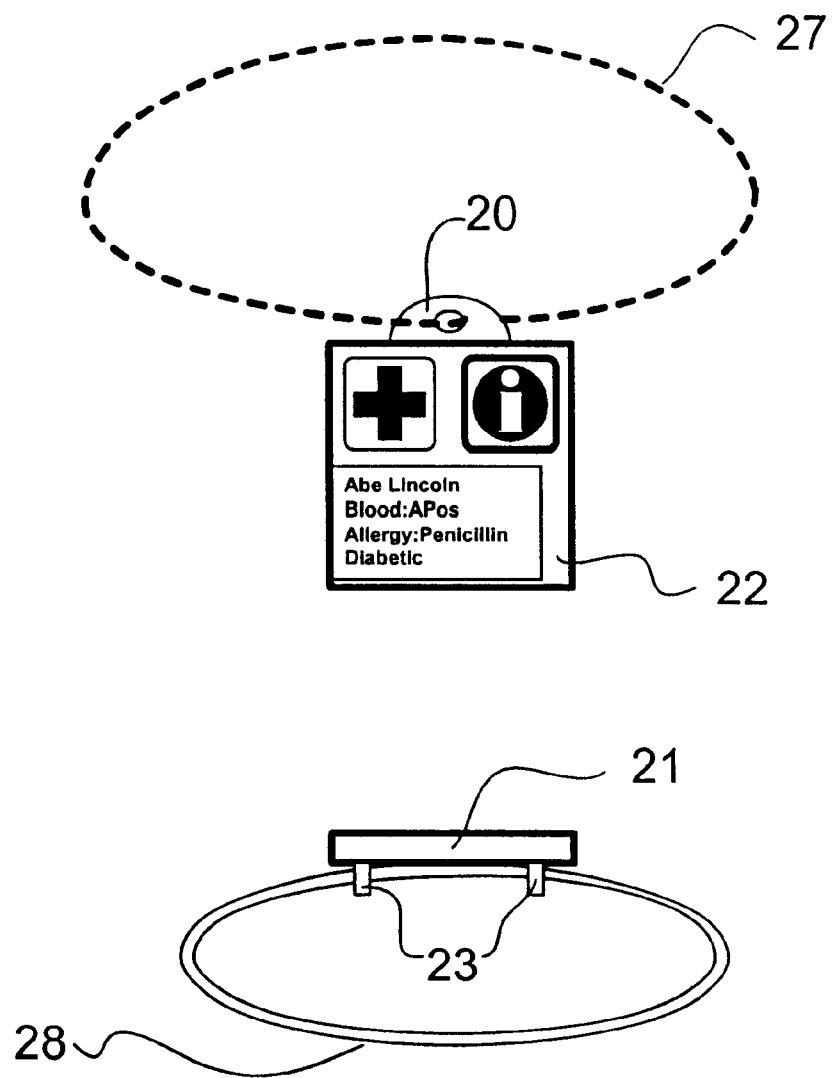
FIG. 7 illustrates a memory card container attached to a necklace and to a wristband.

FIG. 7 shows a top view of the container 22 attached to a necklace 27 via container lug 20. A container side view 21 shows attachment to a wristband 28 via container lugs 23.

Other embodiments would be implemented with a SmartMedia™ card, an Intel® Miniature Card, or other type of memory card instead of a CompactFlash™ card.

Other embodiments could include attachment to ornamental or decorative cases, such as pendants, and cases attached to or an integral part of a timekeeping device, such as a watch.

Jewelry can be attached directly to a memory chip, though the process of attachment or the attachment itself could interfere with operation of the memory chip.

Figure 6:
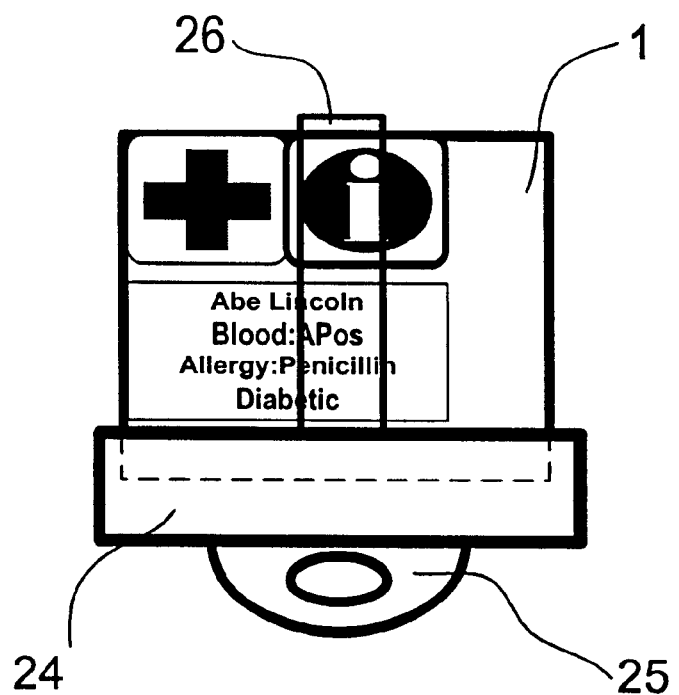
FIG. 6 illustrates a memory card with a protective connector cover with attachment points and surfaces.

Another embodiment has a cover for the memory chip connector or pins, affording some protection without a fully enclosing container. Such a connector cover might be held on with a pressure fit or with a strap around the memory card. Lugs on such a cover or strap provide a means of attachment. FIG. 6 shows a transparent connector cover 24 with an attachment lug 25 and a transparent strap 26.

Other embodiments use symbology on labels appropriate to the bearer's specific needs. For example, a military person's labeling might include the bearer's service number, military branch or affiliation, country, and so forth. United Nations representatives might have a U.N. symbol on their card.

Other embodiments include additional identification means, such as a hair strand, bodily fluid sample or tissue sample containing DNA, a holographic image, a retina scan, or other uniquely identifying feature of the bearer which may be attached to the memory card, its container, attached jewelry, or other attached item.

The foregoing description of the preferred embodiment of the invention has been presented for the purposes of illustration and description. It is not intended to be exhaustive or to limit the invention to the precise forms disclosed. Many modifications and variations are possible in light of the above teaching. It is intended that the scope of the invention be limited not by this detailed description, but rather by the claims appended hereto.

What is claimed is:

1. A reusable electronic data storage device capable of being worn by a bearer comprising:
   a memory card;
   a modifiable directory structure for organizing electronic data files stored in said memory card;
   modifiable electronic files containing bearer information stored in said directory structure;
   labeling on an exterior surface of said memory card indicating a characteristic of the bearer to whom the information pertains;
   a DNA sample from the bearer coupled to the memory card; and
   unique data identifying the bearer retrievably stored on said memory card.

2. The device of claim 1 wherein the memory card has contacts for interfacing with a PCMCIA adapter.

3. The device of claim 2 further comprising a removable cover over the contacts.

4. The device of claim 3 wherein the cover has an aperture for attaching the cover and the memory card to strap worn by the bearer.

5. The device of claim 4 wherein the cover has labeling on an exterior surface of the cover.

6. The device of claim 2 wherein the files are encrypted.

7. The device according to claim 2 wherein the memory device is compliant with the PCMCIA-ATA (Personal Computer Memory Card International Association-AT Attachment) open industry standard.

8. The reusable electronic storage device of claim 1 wherein said information includes medical record information.

9. The reusable electronic storage device of claim 2 wherein said container is operable to protect the memory card from a harsh environment.

10. The device of claim 1 wherein the labeling includes a unique sample from the bearer for verification of identity.

11. A container for a data memory card comprising:
    a generally rectangular housing having a closable opening for receiving a reusable data memory card therein;
    a tab extending from one side of the container for attaching the container to a band so that the container can be worn by a person;
    identification labeling on the container identifying the person to which the data memory card pertains; and a sample of the person's DNA attached to one of the memory card or the container.

12. The container of claim 11 wherein the tab has an aperture therethrough for receiving the band.

13. A reusable electronic storage device comprising:
   a PCMCIA compliant memory card having a plurality of connector contacts;
   a removable cover over the contacts;
   a modifiable directory structure organizing electronic data files stored in the memory card;
   modifiable electronic text, image and data containing medical information stored in said files in said directory structure in said memory card; and
   a DNA sample of a person to which the medical information pertains coupled to the memory card.

14. The device of claim 13 wherein the memory card has contacts for interfacing with a PCMCIA adapter.

15. The device of claim 14 further comprising a removable cover over the contacts.

16. The device of claim 14 wherein the cover has an aperture for attaching the cover and the memory card to strap worn by a bearer.

17. The device of claim 14 wherein the cover has labeling on an exterior surface.

18. The device of claim 13 wherein the files are encrypted.

19. The device of claim 13 further comprising labeling on an exterior surface of the memory card having a unique bearer identifier thereon.

20. The device of claim 19 wherein the identifier is a fingerprint.

* * * * *